(12) United States Patent
Inoue et al.

(10) Patent No.: US 9,221,053 B2
(45) Date of Patent: Dec. 29, 2015

(54) REAGENT CONTAINER

(75) Inventors: Masahide Inoue, Chiba (JP); Minoru Asogawa, Tokyo (JP); Yoshinori Mishina, Saitama (JP)

(73) Assignees: Fujibo Holdings, Inc., Tokyo (JP); NEC Corporation, Tokyo (JP)

( * ) Notice: Subject to any disclaimer, the term of this patent is extended or adjusted under 35 U.S.C. 154(b) by 0 days.

(21) Appl. No.: 14/345,777

(22) PCT Filed: Jul. 10, 2012

(86) PCT No.: PCT/JP2012/067552
§ 371 (c)(1),
(2), (4) Date: Mar. 19, 2014

(87) PCT Pub. No.: WO2013/042435
PCT Pub. Date: Mar. 28, 2013

(65) Prior Publication Data
US 2014/0234185 A1    Aug. 21, 2014

(30) Foreign Application Priority Data
Sep. 20, 2011  (JP) ................................. 2011-204327

(51) Int. Cl.
*B01L 3/00* (2006.01)
*G01N 21/03* (2006.01)
*G01N 1/00* (2006.01)

(52) U.S. Cl.
CPC . *B01L 3/52* (2013.01); *B01L 3/523* (2013.01); *B01L 3/502715* (2013.01);
(Continued)

(58) Field of Classification Search
CPC .................. B01L 3/502715; B01L 2200/0689; B01L 2200/16; B01L 2400/0481; B01L 2200/0605; B01L 2200/0684; B01L 2300/044; B01L 2300/123; B01L 3/52; B01L 2400/0683; G01N 2021/0346; G01N 2001/007
See application file for complete search history.

(56) References Cited

U.S. PATENT DOCUMENTS 4,769,333 A   9/1988  Dole et al.
5,304,348 A   4/1994  Burd et al.
(Continued)

FOREIGN PATENT DOCUMENTS

JP  63 191061  8/1988
JP  7 503794   4/1995
(Continued)

OTHER PUBLICATIONS

International Search Report Issued Sep. 4, 2012 in PCT/JP12/067552 Filed Jul. 10, 2012.
(Continued)

*Primary Examiner* — Dennis M White
(74) *Attorney, Agent, or Firm* — Oblon, McClelland, Maier & Neustadt, L.L.P.

(57) ABSTRACT

A test reagent container includes: a bottom part; a peripheral wall part on the periphery of the bottom part; a storage part which opens upward and with an internal diameter of an inner peripheral wall decreased with depth; a film which seals the opening of the storage part; a discharge channel which penetratingly passes from an inner bottom surface of the storage part to the bottom part of the container body; a projecting part formed downwardly projecting from the bottom part to seal an outlet of the discharge channel; a breakable part including a thick-walled part and a thin-walled part thinner than the thick-walled part formed on the periphery of the projecting part. The breakable part is broken when the projecting part is depressed from outside of the container, the projecting part is inserted into the inside of the discharge channel, and the sealed state of the outlet is released.

8 Claims, 4 Drawing Sheets

(52) U.S. Cl.
CPC ... *B01L 2200/027* (2013.01); *B01L 2200/0605* (2013.01); *B01L 2200/0684* (2013.01); *B01L 2200/0689* (2013.01); *B01L 2200/16* (2013.01); *B01L 2300/044* (2013.01); *B01L 2300/123* (2013.01); *B01L 2400/0481* (2013.01); *B01L 2400/0683* (2013.01); *G01N 2001/007* (2013.01); *G01N 2021/0346* (2013.01)

(56) References Cited

U.S. PATENT DOCUMENTS

| | | |
|---|---|---|
| 2004/0005246 A1 | 1/2004 | Efthimiadis et al. |
| 2004/0241042 A1 | 12/2004 | Pugia et al. |
| 2005/0272169 A1 | 12/2005 | Griffin et al. |
| 2006/0245972 A1 | 11/2006 | Osone et al. |
| 2008/0260581 A1 | 10/2008 | Rosman et al. |
| 2011/0002812 A1* | 1/2011 | Asogawa et al. ............ 422/68.1 |

FOREIGN PATENT DOCUMENTS

| | | |
|---|---|---|
| JP | 2005 512071 | 4/2005 |
| JP | 2006 308366 | 11/2006 |
| JP | 2006 335366 | 12/2006 |
| JP | 2006335366 A * | 12/2006 |
| JP | 2007 500850 | 1/2007 |
| WO | WO 2008/038653 A1 | 4/2008 |
| WO | 2009 035062 | 3/2009 |

OTHER PUBLICATIONS

Extended European Search Report issued Apr. 21, 2015 in Patent Application No. 12833824.1.

* cited by examiner

REAGENT CONTAINER

TECHNICAL FIELD

The present invention relates to a container for sealing a liquid, powdery or gaseous test reagent or the like, and more particularly to a test reagent container where a discharge port can be opened by depressing a projecting member formed on a bottom part of the container so that contents can be reliably discharged.

BACKGROUND ART

Recently, there have been researches on various liquid feeding mechanisms and methods where a filling container and ultrafine flow passages are formed on a piece of microchip, and a sample or a liquid specimen is fed and subjected to reaction under controlled conditions for a gene analysis, a blood examination or the like.

In such an analysis or examination, it is crucial to prevent an artificial error such as the contamination of a sample or a specimen, an error in specimen injection or an error in an amount of test reagent. Particularly when a specimen is used in DNA identification or the like, accuracy and reliability are required in injection of a specimen into an analyzer. To cope with such requirement, patent literature 1 discloses a specimen filling device for injecting a specimen into a microchip. The specimen filling device is mounted with a specimen package having a specimen chamber filled with a specimen, and when a projecting part formed on the specimen chamber is subjected to an external force, a portion of a bottom part is released, thereby discharging the specimen.

This specimen filling device is recognized as effective for preventing an artificial error such as contamination of a specimen, an error in specimen injection or an error in an amount of test reagent. However, the specimen filling device has the following drawback with respect to discharging of a specimen.

That is, in this type of test reagent container, during an operation of discharging a test reagent to the outside by inflating a film with compressed air as shown in FIG. 4(c) of patent literature 1, excessive stretching may break a portion of the film thus preventing sufficient discharge of a test reagent to the outside.

Further, when an amount of test reagent used in an analysis is small, the test reagent liquid may remain in a test reagent chamber, particularly in an inner corner portion formed between a side wall and a bottom part, and may potentially affect the results of the analysis or examination. In view of the above-mentioned circumstances, there has been a demand for a test reagent container where a test reagent can be reliably discharged without remaining in the container even when the amount of test reagent is small.

LIST OF RELATED ART

Patent Literature

PTL 1: Re-publication of PCT International Publication No 2009/035062

SUMMARY OF INVENTION

Technical Problem

Accordingly, the present invention aims to provide a test reagent container which can overcome the above-mentioned drawbacks of the conventional specimen container and can accurately and reliably discharge a small amount of test reagent.

Solution to Problem

The present invention has been made to achieve the above-mentioned aim, and provides a test reagent container which includes: a bottom part; a peripheral wall part which is erected on the periphery of the bottom part; a storage part which opens upward and is formed such that an internal diameter of an inner peripheral wall decreases with depth; a film which seals the opening of the storage part; a discharge channel which passes from an inner bottom surface of the storage part to the bottom part of the container body in a penetrating manner; and a projecting part which is formed in a downwardly projecting manner from the bottom part so as to seal an outlet of the discharge channel, wherein a breakable part composed of a thick-walled part and a thin-walled part thinner than the thick-walled part is formed on the periphery of the projecting part, the breakable part is broken when the projecting part is depressed from the outside of the container, the projecting part is inserted into the inside of the discharge channel, and the sealed state of the outlet is released.

Advantageous Effects of Invention

According to the test reagent container of the present invention, a discharge port for a test reagent can be reliably opened, and a test reagent storage part is formed in a conically recessed shape so that the test reagent can be accurately discharged and prevented from remaining in the container even when the amount of test reagent is small. Further, a film can be prevented from breaking at the time of pushing out the test reagent from the storage part.

BRIEF DESCRIPTION OF DRAWINGS

FIG. 5 (a) A schematic view showing a use mode of the test reagent container of the present invention. (b) A schematic view showing a use mode of the test reagent container of the present invention.

FIG. 6 (a) A schematic view showing thin-walled parts and thick-walled parts of the test reagent container of the present invention in a different mode. (b) A schematic view showing a thin-walled part and a thick-walled part of the test reagent container of the present invention in another different mode. (c) A schematic view showing thin-walled parts and thick-walled parts of the test reagent container of the present invention in still another different mode. (d) A schematic view showing thin-walled parts and thick-walled parts of the test reagent container of the present invention in still another different mode. (e) A schematic view showing thin-walled parts and thick-walled parts of the test reagent container of the present invention in still another different mode.

DESCRIPTION OF EMBODIMENTS

Hereinafter, embodiments of a test reagent container of the present invention are specifically explained by reference to drawings. However, the present invention is not limited to these embodiments.

Figure 1:
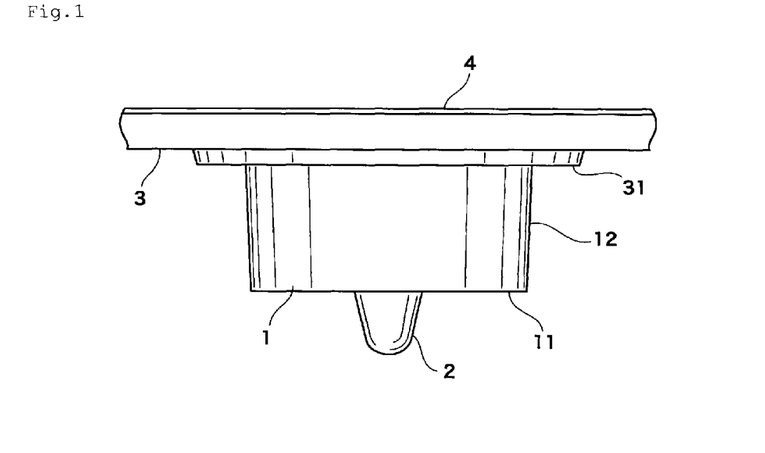
FIG. 1 A side view of a test reagent container of the present invention.
Figure 2:
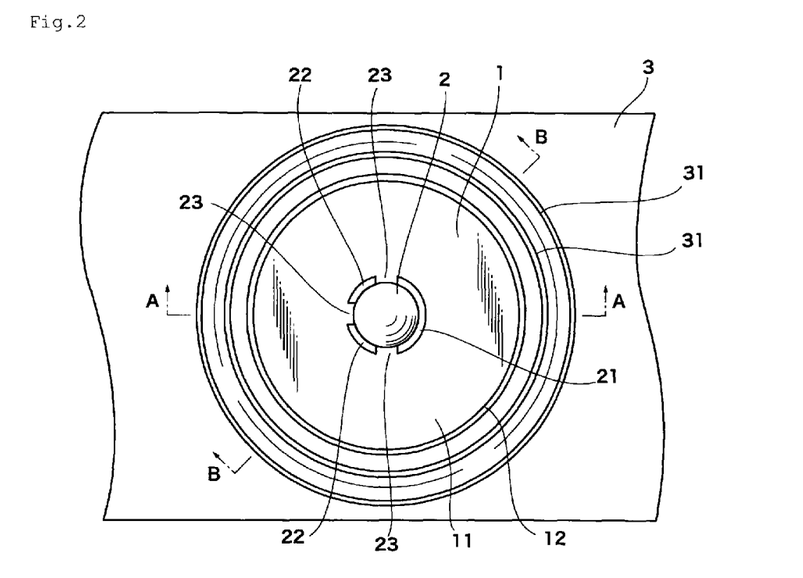
FIG. 2 A bottom view of the test reagent container of the present invention.
Figure 3:
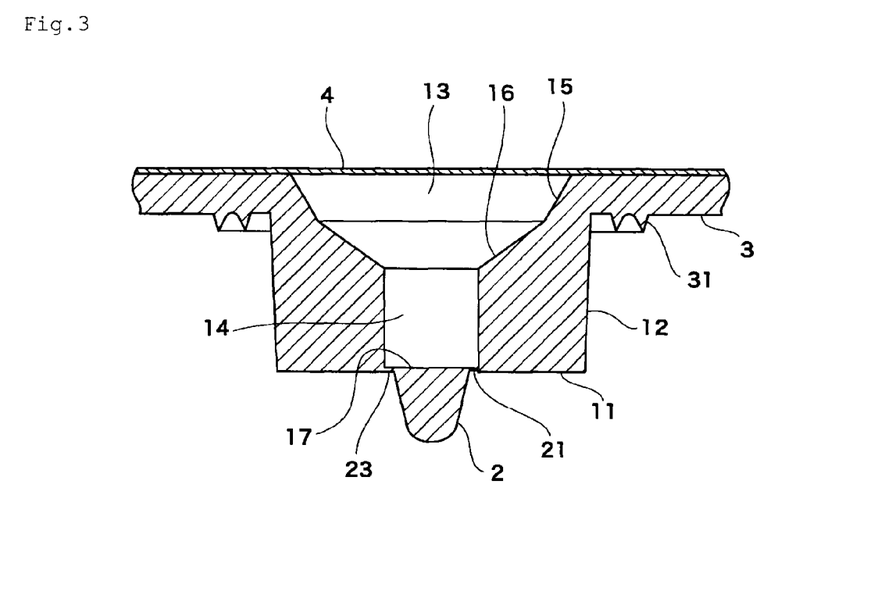
FIG. 3 A cross-sectional view taken along a line A-A of the test reagent container of the present invention.
Figure 4:
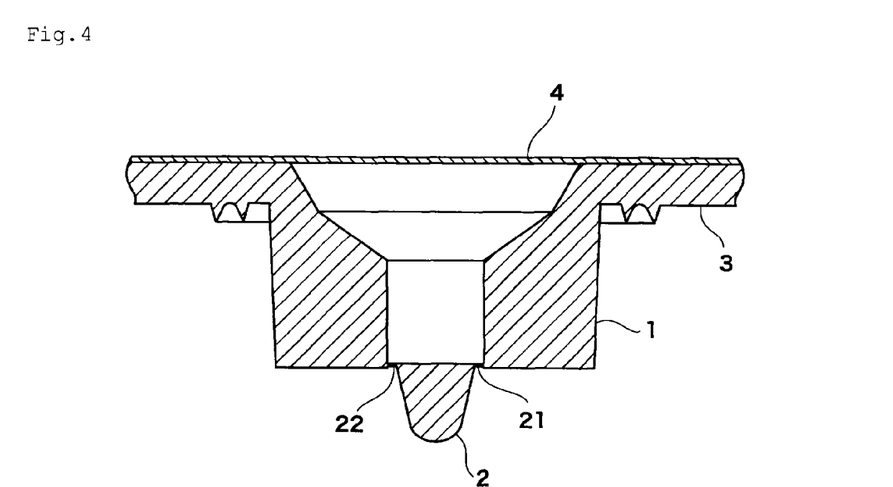
FIG. 4 A cross-sectional view taken along a line B-B of the test reagent container of the present invention.

FIG. 1 is a side view of the test reagent container of the present invention, FIG. 2 is a bottom view of the test reagent container of the present invention, FIG. 3 is a cross-sectional view taken along a line A-A of the test reagent container of the present invention, and FIG. 4 is a cross-sectional view taken along a line B-B of the test reagent container of the present invention. In these drawings, 1 indicates a container body, 2 indicates a projecting part, 3 indicates a flange member, 4 indicates a film, 11 indicates a bottom part, 12 indicates a peripheral wall part, 13 indicates a storage part, 14 indicates a discharge channel, 15 indicates an upper inner wall, 16 indicates a lower inner wall, 17 indicates an outlet of the discharge channel, 21 indicates a thin-walled part, 22 indicates a thin-walled part, 23 indicates a thick-walled part, and 31 indicates annular projecting parts.

As shown in the respective drawings, the test reagent container of the present invention includes a container body 1 which is formed on a plate-like flange member 3 in a downwardly projecting manner. The container body 1 includes a storage part 13 which can store a test reagent or the like therein, and a discharge channel 14 which passes from the storage part 13 to a bottom part 11 of the container in a penetrating manner. In a state where contents are being stored, the upper opening of the storage part 13 is sealed with a film 4, and the outlet of the discharge channel 14 is sealed with a projecting part 2. Hereinafter, the specific constitution of the test reagent container of this embodiment is explained in detail.

The container body 1 of the test reagent container of this embodiment is formed into an inverted truncated cone shape substantially equal to a columnar shape by the bottom part 11 and the peripheral wall part 12 which is erected on the periphery of the bottom part 11. One plate-like flange member 3 extends in the horizontal direction from the upper end of the peripheral wall part 12. The storage part 13 formed in the container body 1 opens upward and is formed into a so-called conically recessed shape such that an internal diameter of an inner wall decreases with depth. The depth of the storage part 13 is approximately ½ of the height of the container body 1. A rate at which the internal diameter decreases with respect to the depth of the storage part 13, that is, an internal diameter decreasing rate with respect to depth may be set at a fixed value. However, as in the case of this embodiment, the internal diameter decreasing rate may differ between the approximately upper half portion and the approximately lower half portion of the storage part 13 in such a manner that the internal diameter decreasing rate in the lower inner wall 16 is greater than in the upper inner wall 15. Preferably, the internal diameter decreasing rate is greater in the lower half portion of the storage part 13 than in the upper half portion so that the film 4 is smoothly stretched along an inner wall at the time of discharging contents by the method to be described later and therefore is prevented from breaking and, at the same time, hardly any reagent remains in the inside of the storage part 13. Instead of adopting two different internal diameter decreasing rates for the upper portion and the lower portion of the inner wall respectively as in the case of this embodiment, the storage part 13 may be formed into a so-called bowl shape such that an internal diameter decreasing rate continuously increases from the upper portion to the lower portion of the inner wall.

The cylindrical discharge channel 14 is formed in the lower half portion of the container body 1 in a vertically penetrating manner. An inlet of the discharge channel 14 is formed at the center of a bottom surface in the inside of the storage part 13, that is, at the center of a bottom of a so-called conically recessed shape, and an outlet of the discharge channel 14 is formed at the center of the bottom part 11 of the container body 1. Accordingly, the portions of the test reagent container of the present invention to store and to discharge a test reagent are formed into a so-called funnel shape which is defined by the storage part 13 formed into a conically recessed shape and the discharge channel 14 arranged below the storage part 13. The projecting part 2 is attached to the outlet 17 of the discharge channel 14 so as to seal the outlet 17. An internal diameter of the discharge channel 14 is not limited particularly and is approximately ⅓ of an outer diameter of the container body 1 in this embodiment. Preferably, the discharge channel 14 has an internal diameter of approximately ⅓ of an outer diameter of the container body 1 so that a wall thickness of the container body 1 around the discharge channel 14 can be increased. Accordingly, the container body 1 and the bottom part 11 can be prevented from being deflected when the projecting part 2 is depressed from below, and a stress can be concentrated on a breakable part with no dispersion.

The projecting part 2 extends downward from the bottom part 11 of the container body 1 in a projecting manner and is formed into a truncated cone shape with a rounded distal end. A breakable part composed of thin-walled parts 21, 22 and thick-walled parts 23 is formed on the periphery of the projecting part 2. The projecting part 2 is joined to a portion of the bottom part 11 by way of the breakable part. In a bottom view shown in FIG. 2, the thick-walled parts 23 are formed on the periphery of the projecting part 2 at three positions in total, that is, at the upper side, at the lower side and at the left side of the projecting part 2. The thin-walled parts 22 are formed at two positions between the upper and lower thick-walled parts 23 and the left thick-walled part 23, and the thin-walled part 21 is formed on the periphery of the projecting part 2 at one position, that is, at the right of the upper and lower thick-walled parts 23. This means that the thin-walled parts are formed at three positions in total. The thin-walled parts 21, 22 are thinner than the thick-walled parts 23, and the thin-walled part 21 is longer than the thin-walled part 22 and extends over approximately ½ of the length of the whole periphery of the projecting part 2. In this manner, the thin-walled part 21 constitutes a most easily breakable part among all breakable parts. A thickness t1 of the thin-walled part 21, 22 and a thickness t2 of the thick-walled part 23 are not particularly limited provided that the breaking starts from the thin-walled part when the projecting part 2 is depressed from below. In view of the ease of breaking and the sealing property, the preferable range is $0.03 < t1 < 0.1$ mm for the thin-walled part and $0.06 < t2 < 0.2$ mm for the thick-walled part where the relationship of $t1 < t2$ is satisfied. The range of preferable width is $0 < w \leq 1$ mm both for the thin-walled parts 21, 22 and the thick-walled part 23. The length of the thin-walled parts 21, 22 and the length of the thick-walled part 23 are not particularly limited provided that the breaking starts from the thin-walled part 21. In order to start the breaking from the thin-walled part 21 smoothly, it is preferable that the thin-walled part 21 is continuously formed so as to extend over ¼ or more of the length of the whole periphery of the projecting part 2. On the other hand, a length L of the thick-walled part 23 is preferably $0.06 < L$ mm.

Figure 6:
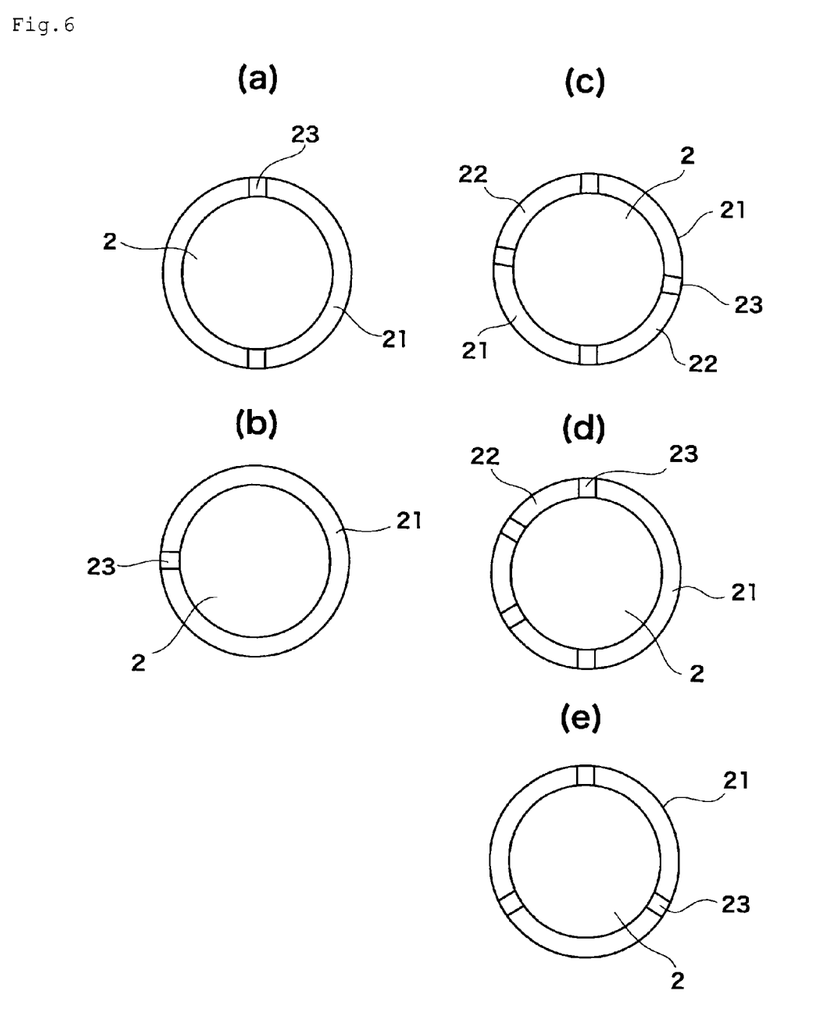

The number and positions of the thin-walled parts and the thick-walled parts are not particularly limited. As in the case of this embodiment, it is preferable that the thin-walled parts and the thick-walled parts are formed at three positions respectively and one thin-walled part among three thin-walled parts is continuously formed so as to extend over ¼ or more of the length of the whole periphery of the projecting part 2. In this manner, both the ease in opening the discharge channel outlet 17 and the sealing property using the projecting part 2 can be achieved. Modes of different number and positions of the thin-walled parts and the thick-walled parts are shown in FIG. 6(*a*) to FIG. 6(*e*). The thick-walled part 23 may be formed on the periphery of the projecting part 2 at one, two, three or four positions, and the thin-walled part 21 may be continuously formed so as to extend over ¼ or more of the length of the whole periphery of the projecting part 2.

The projecting part 2 is arranged such that a portion having the maximum projection height is positioned at the central portion of the bottom part 11 of the container body 1. Due to such a constitution, when the projecting part 2 is depressed from below, a stress is uniformly dispersed on the periphery of the projecting part 2 and hence, the breaking surely starts from the thin-walled part 21. Although the projecting part 2 has a truncated cone shape with the rounded distal end in this embodiment, the projecting part 2 is not necessarily formed into such a shape, and may have a circular shape including an elliptical shape, a triangular shape, a quadrangular shape which includes a trapezoidal shape or the like as viewed in a bottom plan view.

Figure 5:
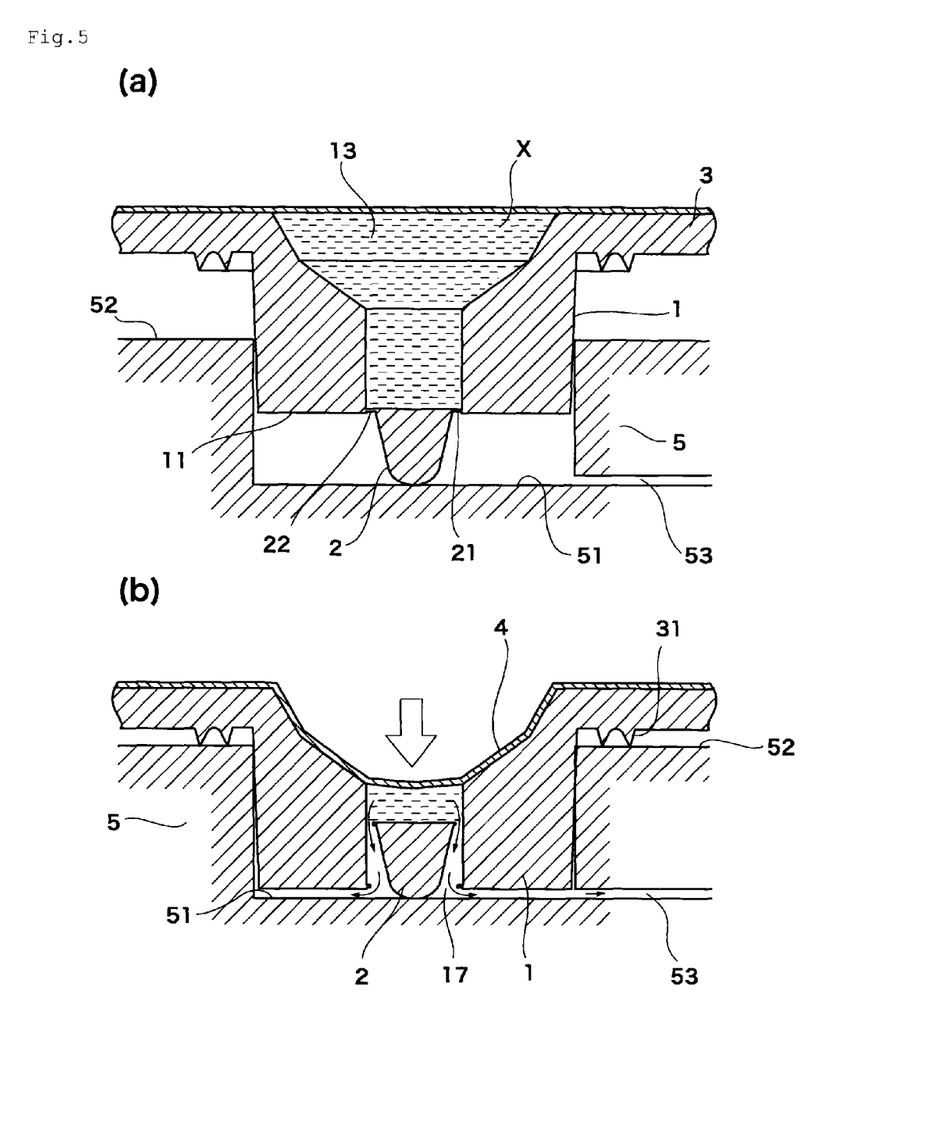

When the breakable part arranged on the periphery of the projecting part 2 is completely broken, the projecting part 2 is pushed into the inside of the discharge channel 14. When the projecting part 2 is inserted into the inside of the discharge channel 14 in this manner, a sealed state of the discharge channel outlet 17 is released so that a test reagent can be discharged. The inserted projecting part 2 remains in the inside of the discharge channel 14 and hence, there is no possibility that the projecting portion returns to an original position and closes the outlet during an operation of discharging thus obstructing the discharge of the test reagent. There is also no possibility that the projecting part 2 obstructs the stretching of the film 4 in the inside of the storage part 13. The discharge channel 14 need not necessarily be formed at the center axis of the container body 1 as in this embodiment, and may be formed eccentrically in any one direction from the center axis of the container body 1 toward a peripheral wall side. An advantageous effect brought about by not forming the discharge channel 14 at the center of the container body 1 is as follows. That is, to discharge a test reagent from the container, as shown in FIG. 5(*b*), the film 4 is inflated in the inside of the storage part 13 by an air pressure applied from above so that the contents are forcibly discharged from the storage part 13. After the inflation in the inside of the storage part 13, the film 4 may be further inflated and may intrude into the inside of the discharge channel 14 depending on the relationship between the air pressure and the stretchability of the film 4. In such a case, the film 4 is already in a fully stretched state at the center of the bottom surface of the storage part 13 and hence, the further stretching of the film 4 may cause breaking of the film per se. In this respect, by forming the discharge channel 14 eccentrically in any one direction from the center axis of the container body 1, the inlet of the discharge channel 14 is positioned at a portion where the film 4 is not yet fully stretched and hence, even when the film 4 is further inflated and intrudes into the inside of the discharge channel 14, there is no possibility that the film 4 breaks. Accordingly, breaking of the film during the discharge operation can be prevented.

A material used for forming the container is not particularly limited provided that the material has the necessary and sufficient sealing property for preserving a test reagent as well as hardness to such an extent that the breakable part is easily broken. As a material which satisfies these conditions, an EVA resin, a low-density PE or the like can be preferably used.

With respect to the film 4 which seals the opening of the storage part 13, it is preferable to use a film having a barrier property to an enzyme or a specific chemical such as an alcohol and having stretchability to some extent. To be more specific, an EVOH film, a PE film, an LLDPE film or the like can be preferably used as the film 4. To further enhance a gas barrier property, a film having a barrier function may be laminated to the above-mentioned film in a peelable manner, and the film having a barrier function may be removed at the time of using the film 4. As such a film having a barrier function, an aluminum film or the like can be preferably used.

FIG. 5 shows a mode of a use state of the test reagent container of the present invention. The test reagent container of the present invention filled with a test reagent X is mounted in a cartridge 5 for analysis of a microchip or the like. A recessed part 51 in which the test reagent container can be mounted is formed in the cartridge 5, and a flow passage 53 for delivering a test reagent from a bottom part of the recessed part 51 is formed in the cartridge 5 in an extended manner. The recessed part 51 has a depth equal to or substantially equal to a height of the peripheral wall part 12 of the container body 1. Hereinafter, a process flow of an operation of mounting the test reagent container is explained.

Firstly, the container body 1 is inserted into the inside of the recessed part 51 from a bottom part 11 side as is. Alternatively, when a film having a barrier function is laminated to the film 4, the film having a barrier property is removed from the film 4, and then the container body 1 is inserted into the inside of the recessed part 51 from a bottom part 11 side. At this point in time, a distal end of the projecting part 2 is brought into in contact with the bottom part of the recessed part 51 and prevents the container body 1 from being completely inserted into the inside of the recessed part 51 so that a gap is formed between the bottom part 11 and the recessed part 51 as shown in FIG. 5(*a*). Next, the container body is covered with a cover member or the like from above, and a downward pressure is applied to the test reagent container. Due to such depressing, an upward stress acts on the projecting part 2 which is in contact with the bottom part of the recessed part 51 and hence, breaking of the breakable part formed on the periphery of the projecting part 2 starts from the thin-walled part 21. When the depressing is continued under the same condition, the thin-walled part 22 is then broken, and finally, the thick-walled part 23 is broken. Due to the completion of the breaking of the breakable part, the projecting part 2 is separated from the bottom part 11 and is inserted into the inside of the discharge channel 14. Then, the container body 1 is further deeply inserted into the inside of the recessed part 51, and the mounting operation is completed at a point in time when the annular projecting part 31 is brought into contact with the upper surface 52 of the cartridge 5 as shown in FIG. 5(*b*). In this embodiment, the breakable part is completely broken and hence, the projecting part 2 is separated from the bottom part 11 and is inserted into the inside of the discharge channel 14 with little change in posture. Alternatively, the breakable part may be broken leaving some thick-walled parts so that the projecting part 2 is inserted into the inside of the discharge channel 14 in an inclined manner with respect to the thick-walled part which serves as a supporting point thus ensuring the discharge channel outlet.

In this manner, by breaking the breakable part at the time of mounting the test reagent container in the analyzer, a sealed state of the outlet 17 of the discharge channel 14 formed by the projecting part 2 is released, and a test reagent which is the content is discharged to the outside of the container through the gap formed between the discharge channel 14 and the projecting part 2 as indicated by the arrow in the drawing. Although the content may be discharged in such a manner that the content flows out naturally, to discharge a test reagent more effectively without leaving the test reagent in the storage part 13, as shown in FIG. 5(b), it is preferable to forcibly discharge the content by applying an air pressure to the film 4 from above and inflating the film 4 in the inside of the storage part 13. By the air pressure, the film 4 is inflated in a shape which approximately conforms to a shape of the inside of the storage part 13. Since the film 4 is stretched smoothly, the film 4 can be prevented from breaking when inflated, and at the same time, the test reagent can be discharged without the slightest amount left in the storage part 13.

Further, in the test reagent container of this embodiment, annular projecting parts 31 are formed on a lower surface of the flange member 3 in a state where the annular projecting parts 31 surround the peripheral wall part 12 doubly. Peak portions of the annular projecting parts 31 are brought into contact with a ceiling surface 52 of the cartridge 5 when the test reagent container is inserted into the recessed part 51. Due to the formation of the annular projecting parts 31, even when the content exudes through a gap formed between the peripheral wall part 12 and the recessed part 51, the content is sealed in at the annular projecting parts 31 and hence, the contamination of a test reagent or the like can be effectively prevented without using a sealing member such as an O-ring. To further enhance such a sealing effect, a film made of an elastic material such as a silicon film (not shown in the drawing) may be laminated to the ceiling surface of the cartridge 5. By laminating such an elastic film to the ceiling surface of the cartridge 5, when the test reagent container 1 is mounted in the cartridge 5, the peak portions of the annular projecting parts 31 bite into the elastic film and hence, the sealing property of the annular projecting parts 31 can be further enhanced. Further, separately from the annular projecting parts 31 or together with the annular projecting parts 31, an annular projecting part (not shown in the drawing) which extends outwardly in a projecting manner may be formed on an outer peripheral surface of the peripheral wall part 12 of the test reagent container 1. Thus, even when the content exudes through a fine gap formed between the test reagent container 1 and the recessed part 51, the content is sealed in at the annular projecting part which is in contact with the inner peripheral wall of the recessed part 51. Accordingly, it is preferable to form such an annular projecting part.

The test reagent container 1 according to the present invention may be configured such that a plurality of containers 1 are contiguously arranged. In such a case, the containers arranged adjacent to each other may be interconnected by a flange member 3. For example, when the test reagent container 1 is formed of an eight-tandem container, eight test reagent containers 1 are joined to each other using one sheet of flange member 3. The eight-tandem container may be used in such a manner that seven containers among these containers are filled with a test reagent in advance, and the eighth container is filled with a collected sample.

When the test reagent X is a content in the form of liquid, it is possible to control the localization of air bubbles generated at the time of discharging the test reagent X by controlling the wettability of respective front surface parts of the projecting part 2, the bottom part of the recessed part 51, the bottom part 11 and the peripheral wall part 12 with the test reagent X. For example, by maintaining favorable wettability of respective surfaces of the projecting part 2, the bottom part of the recessed part 51 and the bottom part 11 with the test reagent X, the discharged test reagent X is developed in a state where contact angles made by the test reagent X and the respective surfaces of the projecting part 2, the bottom part of the recessed part 51 and the bottom part 11 are kept small. In this manner, the gap formed by the projecting part 2, the bottom part of the recessed part 51 and the bottom part 11 can be filled with the test reagent X without generating air bubbles. Accordingly, the test reagent X can be fed into a next test reagent vessel through the flow passage 53 without air bubbles.

INDUSTRIAL APPLICABILITY

The test reagent container of the present invention is most preferably applied to a content in the form of liquid. However, the test reagent container of the present invention is also applicable to a content in other form such as a powdery form and a gaseous form. Further, the use of the test reagent container of the present invention is not limited to the filling of a test reagent into an analyzing/inspection device, and the test reagent container of the present invention can be used widely as long as the property that the content is reliably discharged by depressing from the outside can be utilized.

REFERENCE SIGNS LIST

1: container body
2: projecting part
3: flange member
4: film
5: cartridge
11: bottom part
12: peripheral wall part
13: storage part
14: discharge channel
15: upper inner wall
16: lower inner wall
17: discharge channel outlet
21: thin-walled part
22: thin-walled part
23: thick-walled part
31: annular projecting part
51: recessed part
52: ceiling surface
53: flow passage
X: test reagent

The invention claimed is:
1. A test reagent container comprising:
a bottom part;
a peripheral wall part which is erected on a periphery of the bottom part;
a storage part which opens upward and is formed such that an internal diameter of an inner peripheral wall is continuously decreased with depth from an upper portion to a lower portion of the inner peripheral wall;
a stretchable film which seals an opening of the storage part and is pressurizable from an outside of the container;
a discharge channel which passes from an inner bottom surface of the storage part to the bottom part of the container in a penetrating manner; and
a projecting part which is formed in a downwardly projecting manner from the bottom part so as to seal an outlet of the discharge channel, wherein
a breakable part composed of a thick-walled part and a thin-walled part thinner than the thick-walled part is formed on a periphery of the projecting part, the breakable part is broken when the projecting part is depressed from the outside of the container, the projecting part is inserted into an inside of the discharge channel without reaching the storage part, a sealed state of the outlet is released, and wherein the film is inflatable into the storage part thereby discharging a content of the container and extendable to the inner bottom surface of the storage part without reaching the discharge channel.

2. The test reagent container according to claim 1, wherein the thin-walled part is continuously formed so as to extend over ¼ or more of a length of the whole periphery of the projecting part.

3. The test reagent container according to claim 1, wherein the thin-walled part is formed on the periphery of the projecting part at a plurality of positions, and at least one of the thin-walled part is continuously formed so as to extend over ¼ or more of length of the whole periphery of the projecting part.

4. The test reagent container according to claim 1, wherein an internal diameter decreasing rate is greater in the lower portion than in the upper portion of the inner peripheral wall of the storage part.

5. The test reagent container according to claim 1, wherein a thickness of the thin-walled part falls within a range of $0.03<t1<0.1$ mm, a thickness of the thick-walled part falls within a range of $0.06<t2<0.2$ mm, a width of the thin-walled part falls within a range of $0<w\leq1$ mm, and a width of the thick-walled part falls within a range of $0<w\leq1$ mm.

6. The test reagent container according to claim 1, wherein the discharge channel is formed eccentrically in any one direction from a center axis of the container toward a peripheral wall side.

7. The test reagent container according to claim 1, wherein a flange member is formed on an upper end of the peripheral wall part in a projecting manner, the film is attached onto an upper surface of the flange member so as to seal a container opening part.

8. The test reagent container according claim 7, wherein an annular projecting part is formed on a lower surface of the flange member around the peripheral wall part.

* * * * *